US012678139B2

(12) United States Patent (10) Patent No.: US 12,678,139 B2
Venkataramani et al. (45) Date of Patent: Jul. 14, 2026

---

(54) SYSTEMS AND METHODS FOR UNCERTAINTY AWARE CALIPER PLACEMENT

(71) Applicant: GE Precision Healthcare LLC, Waukesha, WI (US)

(72) Inventors: Rahul Venkataramani, Bangalore (IN); Krishna Seetharam Shriram, Bangalore (IN); Chandan Kumar Mallappa Aladahalli, Bangalore (IN); Christian Fritz Perrey, Linz (AT); Michaela Hofbauer, Linz (AT)

(73) Assignee: GE Precision Healthcare LLC, Wauwatosa, WI (US)

( * ) Notice: Subject to any disclaimer, the term of this patent is extended or adjusted under 35 U.S.C. 154(b) by 270 days.

(21) Appl. No.: 18/449,088

(22) Filed: Aug. 14, 2023

(65) Prior Publication Data

US 2025/0057508 A1 Feb. 20, 2025

(51) Int. Cl.
*A61B 8/00* (2006.01)

(52) U.S. Cl.
CPC ............ *A61B 8/469* (2013.01); *A61B 8/5284* (2013.01)

(58) Field of Classification Search
CPC .................... G06F 40/40; G06T 11/00; G06T 2207/10132; G06T 2207/20081; G06T 2207/20084; G06T 7/0012; G06T 7/11; G06T 7/12; G06V 10/82; G06V 10/761; G06V 10/774; A61B 8/469; A61B 8/5284; A61B 8/5223; A61B 8/0841; A61B 8/4488; A61B 5/1075; A61B 8/461; A61B 8/48; A61B 8/486; A61B 8/488; G16H 30/20
See application file for complete search history.

(56) References Cited

U.S. PATENT DOCUMENTS

2020/0265577 A1* 8/2020 Khallaghi ............... G06T 7/155
2022/0338842 A1* 10/2022 Shin ..................... A61B 8/5215
2022/0343494 A1* 10/2022 Dhatt ..................... A61B 8/468

FOREIGN PATENT DOCUMENTS

EP 3596699 B1 * 12/2020 ........... A61B 8/5223

OTHER PUBLICATIONS

Karimi, Davood, et al. "Accurate and robust deep learning-based segmentation of the prostate clinical target volume in ultrasound images." Medical image analysis 57 (2019): 186-196. (Year: 2019).*

(Continued)

*Primary Examiner* — Daniel F Hajnik
(74) *Attorney, Agent, or Firm* — Fletcher Yoder, P.C.

(57) ABSTRACT

Systems and methods for characterizing uncertainty on a boundary of a region of interest includes inputting, via a processor, an ultrasound image having the region of interest into a trained neural network. Systems and methods also include outputting, via the processor, from the trained neural network a first prediction of the boundary of the region of interest and a second prediction of a region segmentation of the region of interest. Systems and methods further include determining, via the processor, an uncertainty on the boundary based on mismatch between the first prediction and the second prediction.

12 Claims, 12 Drawing Sheets

(56) References Cited

OTHER PUBLICATIONS

Dhombres, Ferdinand, et al. "Relation between the quality of the ultrasound image acquisition and the precision of the measurement of the crown-rump length in the late first trimester: what are the consequences?." European Journal of Obstetrics & Gynecology and Reproductive Biology 207 (2016): 37-44. (Year: 2016).*

Cao et al., Learning Crisp Boundaries Using Deep Refinement Network and Adaptive Weighting Loss, IEEE, 11 pgs.

Yeung et al., "Incorporating Boundary Uncertainty Into Loss Functions for Biomedical Image Segmentation," Oct. 2021, EESS IV, 5 pgs.

Mukhoti et al., "Deep Deterministic Uncertainty for Semantic Segmentation," ICML Workshop on Uncertainty and Robustness in Deep Learning, Oct. 29, 2021, 5 pgs.

* cited by examiner

SYSTEMS AND METHODS FOR UNCERTAINTY AWARE CALIPER PLACEMENT

BACKGROUND

The subject matter disclosed herein relates to ultrasound image processing and, more particularly, systems and methods for uncertainty aware caliper placement.

An ultrasound device may be used for imaging targets such as organs and soft tissues in a human body, as well non-human targets. For example, an ultrasound device may be used for applications such as ultrasound/acoustic sensing, non-destructive evaluation (NDE), ultrasound therapy (e.g., High Intensity Focused Ultrasound (HIFU)), etc., in addition to ultrasound imaging of humans, animals, etc.

Ultrasound devices may use real time, non-invasive high frequency sound waves to produce a series of two-dimensional (2D) and/or three-dimensional (3D) images. The sound waves may be transmitted by a transmit transducer, and the reflections of the transmitted sound waves may be received by a receive transducer. The received sound waves may then be processed to display an image of the target. Calipers are placed on the ultrasound image to enable measurement of a target. Caliper placement on ultrasound images for biometry is a task that has been automated in multiple contexts. The calipers are usually placed on the outer bounds of a region of interest. Region segmentation often encounters uncertainties at the margins of the region of interest and therefore caliper locations can be placed in less than desirable locations. The less than desirable locations may be shadow regions in the ultrasound images or regions with low image gradients.

BRIEF DESCRIPTION

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In one embodiment, a computer-implemented method for characterizing uncertainty on a boundary of a region of interest is provided. The computer-implemented method includes inputting, via a processor, an ultrasound image having the region of interest into a trained neural network. The computer-implemented method also includes outputting, via the processor, from the trained neural network a first prediction of the boundary of the region of interest and a second prediction of a region segmentation of the region of interest. The computer-implemented method further includes determining, via the processor, an uncertainty on the boundary based on mismatch between the first prediction and the second prediction.

In one embodiment, the computer-implemented method includes providing, via the processor, a user-perceptible indication of the uncertainty when mismatch is present between the first prediction and the second prediction.

In one embodiment, providing the user-perceptible indication of the uncertainty include indicating on the ultrasound image any region of uncertainty on the boundary.

In one embodiment, the user-perceptible indication includes highlighting the region of uncertainty on the ultrasound image.

In one embodiment, the computer-implemented method includes automatically placing, via the processor, a pair of calipers on the region of interest in the ultrasound image in an absence of uncertainty on the boundary.

In one embodiment, the ultrasound image includes a pair of calipers marked on the region of interest.

In one embodiment, the computer-implemented method includes providing, via the processor, an alert to a user when at least a portion of the pair of calipers is placed in a region of uncertainty on the boundary.

In one embodiment, the computer-implemented method includes providing, via the processor, a user-perceptible indication on the ultrasound image of any end of the caliper placed in a region of uncertainty on the boundary.

In one embodiment, the user-perceptible indication includes having any end of the pair of calipers in the region of uncertainty shown as a different color from the rest of the pair of calipers.

In one embodiment, the computer-implemented method includes altering, via the processor, placement of the pair of calipers on the region of interest in the ultrasound image when at least a portion of the pair of calipers is placed in a region of uncertainty on the boundary.

In another embodiment, a system for characterizing uncertainty on a boundary of a region of interest is provided. The system includes a memory encoding processor-executable routines. The system also includes a processor configured to access the memory and to execute the processor-executable routines, wherein the routines, when executed by the processor, cause the processor to perform actions. The actions include inputting an ultrasound image having the region of interest into a trained neural network. The actions also include outputting from the trained neural network a first prediction of the boundary of the region of interest and a second prediction of a region segmentation of the region of interest. The actions further include determining an uncertainty on the boundary based on mismatch between the first prediction and the second prediction.

In one embodiment, the actions include providing a user-perceptible indication of the uncertainty when mismatch is present between the first prediction and the second prediction.

In one embodiment, providing the user-perceptible indication of the uncertainty includes indicating on the ultrasound image any region of uncertainty on the boundary.

In one embodiment, the actions include causing the processor to automatically place a pair of calipers on the region of interest in the ultrasound image in an absence of uncertainty on the boundary.

In one embodiment, the ultrasound image includes a pair of calipers marked on the region of interest.

In one embodiment, the actions include causing the processor to provide an alert to a user when at least a portion of the pair of calipers is placed in a region of uncertainty on the boundary.

In one embodiment, the actions include providing a user-perceptible indication on the ultrasound image of any end of the pair of calipers placed in a region of uncertainty on the boundary.

In one embodiment, the user-perceptible indication includes having any end of the pair of calipers in the region of uncertainty shown as a different color from the rest of the pair of calipers.

In one embodiment, the actions include causing the processor to alter placement of the pairs of calipers on the region of interest in the ultrasound image when at least a portion of the pair of calipers is placed in a region of uncertainty on the boundary.

In a further embodiment, a non-transitory computer-readable medium, the computer-readable medium including a processor-executable code that when executed by a processor, causes the processor to perform actions. The actions include inputting a medical image having the region of interest into a trained neural network. The actions also include outputting from the trained neural network a first prediction of the boundary of the region of interest and a second prediction of a region segmentation of the region of interest. The actions further include determining an uncertainty on the boundary based on mismatch between the first prediction and the second prediction.

In one embodiment, the actions including providing a user-perceptible indication of the uncertainty when mismatch is present between the first prediction and the second prediction.

In one embodiment, providing the user-perceptible indication of the uncertainty includes indicating on the ultrasound image any region of uncertainty on the boundary.

In one embodiment, the actions include causing the processor to automatically place a pair of calipers on the region of interest in the ultrasound image in an absence of uncertainty on the boundary.

In one embodiment, the ultrasound image includes a pair of calipers marked on the region of interest.

In one embodiment, the actions include causing the processor to provide an alert to a user when at least a portion of the pair of calipers is placed in a region of uncertainty on the boundary.

In one embodiment, the actions include providing a user-perceptible indication on the ultrasound image of any end of the pair of calipers placed in a region of uncertainty on the boundary.

In one embodiment, the user-perceptible indication includes having any end of the pair of calipers in the region of uncertainty shown as a different color from the rest of the pair of calipers.

In one embodiment, the actions include causing the processor to alter placement of the pairs of calipers on the region of interest in the ultrasound image when at least a portion of the pair of calipers is placed in a region of uncertainty on the boundary.

BRIEF DESCRIPTION OF THE DRAWINGS

These and other features, aspects, and advantages of the present subject matter will become better understood when the following detailed description is read with reference to the accompanying drawings in which like characters represent like parts throughout the drawings, wherein.

DETAILED DESCRIPTION

Figure 1:
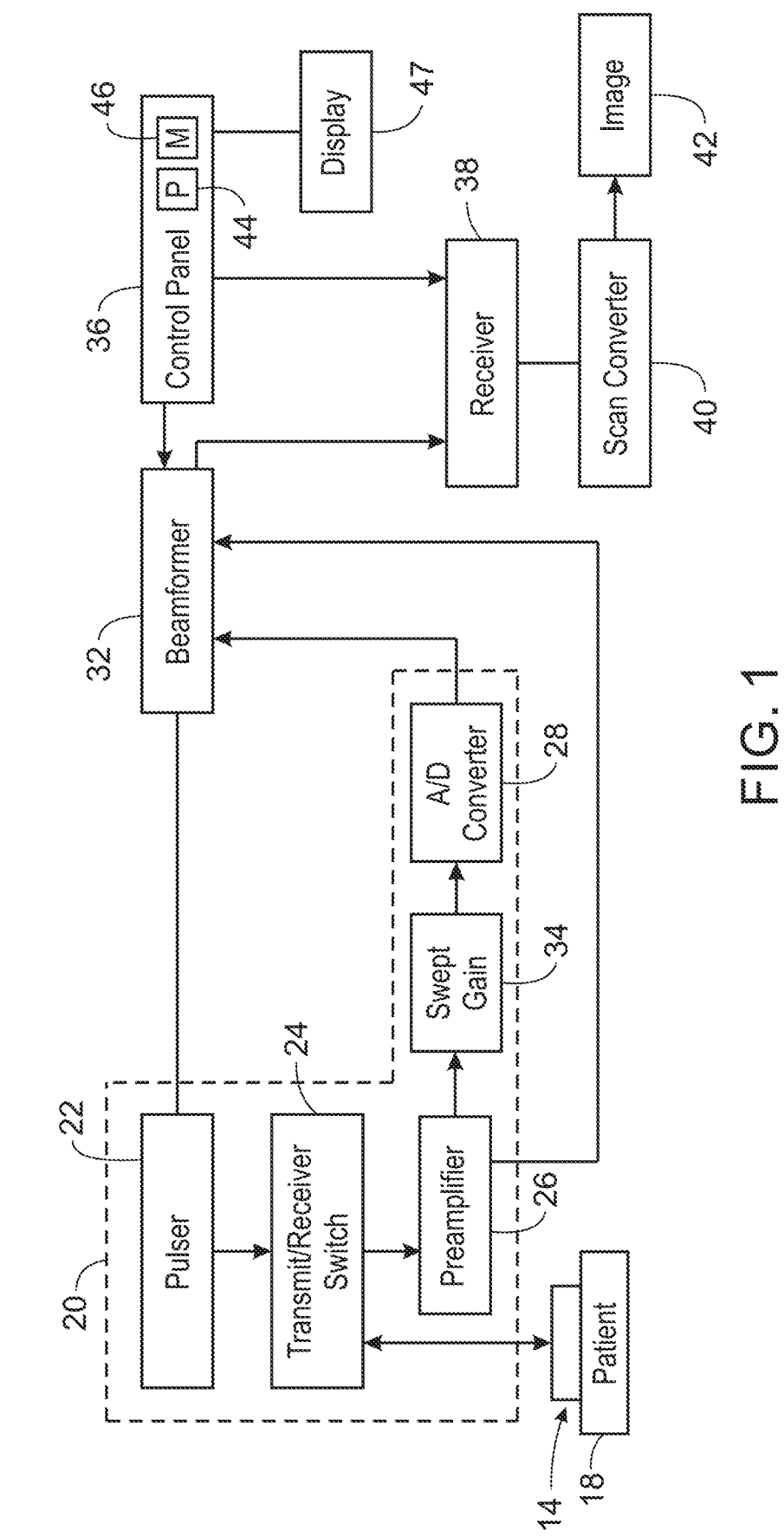
FIG. 1 is an embodiment of a block diagram of an ultrasound system, in accordance with aspects of the present disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with systemrelated and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

Some generalized information is provided to provide both general context for aspects of the present disclosure and to facilitate understanding and explanation of certain of the technical concepts described herein.

As used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode (2D mode), M-mode, three-dimensional (3D) mode, CF-mode, PW Doppler, CW Doppler, MGD, and/or sub-modes of B-mode and/or CF such as Shear Wave Elasticity Imaging (SWEI), TVI, Angio, B-flow, BMI, BMI_Angio, and in some cases also MM, CM, TVD where the "image" and/or "plane" includes a single beam or multiple beams.

Furthermore, the term processor or processing unit, as used herein, refers to any type of processing unit that can carry out the required calculations needed for the various embodiments, such as single or multi-core: CPU, Accelerated Processing Unit (APU), Graphics Board, DSP, FPGA, ASIC or a combination thereof.

Deep-learning (DL) approaches discussed herein may be based on artificial neural networks, and may therefore encompass one or more of deep neural networks, fully connected networks, convolutional neural networks (CNNs), unrolled neural networks, perceptrons, encoders-decoders, recurrent networks, transformer networks, wavelet filter banks, u-nets, general adversarial networks (GANs), dense neural networks (e.g., residual dense networks (RDNs), or other neural network architectures. The neural networks may include shortcuts, activations, batch-normalization layers, and/or other features. These techniques are referred to herein as deep-learning techniques, though this terminology may also be used specifically in reference to the use of deep neural networks, which is a neural network having a plurality of layers.

As discussed herein, deep-learning techniques (which may also be known as deep machine learning, hierarchical learning, or deep structured learning) are a branch of machine learning techniques that employ mathematical representations of data and artificial neural networks for learning and processing such representations. By way of example, deep-learning approaches may be characterized by their use of one or more algorithms to extract or model high level abstractions of a type of data-of-interest. This may be accomplished using one or more processing layers, with each layer typically corresponding to a different level of abstraction and, therefore potentially employing or utilizing different aspects of the initial data or outputs of a preceding layer (i.e., a hierarchy or cascade of layers) as the target of the processes or algorithms of a given layer. In an image processing or reconstruction context, this may be characterized as different layers corresponding to the different feature levels or resolution in the data. In general, the processing from one representation space to the next-level representation space can be considered as one 'stage' of the process. Each stage of the process can be performed by separate neural networks or by different parts of one larger neural network.

The present disclosure provides for systems and methods for characterizing uncertainty on a boundary of a region of interest. In particular, the disclosed systems and methods include inputting an ultrasound image having the region of interest into a trained neural network. The disclosed systems and methods also include outputting from the trained neural network a first prediction of the boundary of the region of interest and a second prediction of a region segmentation of the region of interest. The disclosed systems and methods further include determining an uncertainty on the boundary based on mismatch between the first prediction and the second prediction. In certain embodiments, the disclosed systems and methods includes providing a user-perceptible indication of uncertainty when present between the first prediction and the second prediction. This may include indicating on the ultrasound image any region of uncertainty on the boundary. In certain embodiments, the disclosed systems and methods include automatically placing a pair of calipers on the region of interest in the ultrasound image in the absence of uncertainty on the boundary.

It should be noted that although the disclosed techniques are described with respect to ultrasound images, the disclosed techniques may be utilized with medical images obtained from other imaging modalities (e.g., magnetic resonance imaging (MRI), nuclear medicine (NM) imaging, computed tomography (CT) imaging, conventional X-ray imaging, etc.).

In certain embodiments, the inputted ultrasound image may include a pair of calipers placed or marked on the region of interest. In this scenario, in certain embodiments, the disclosed system and method include providing an alert to a user when at least a portion of the pair of calipers is placed in a region of uncertainty on the boundary. In certain embodiments, the disclosed system and method include providing a user-perceptible indication on the ultrasound image of any end of the pair of calipers placed in a region of uncertainty on the boundary. For example, any end of the pair of calipers in the region of uncertainty a different color from the rest of the pair of calipers. In another example, the region of uncertainty itself may be highlighted on the ultrasound image. In certain embodiments, the disclosed system and method include altering placement of the pair of calipers on region of interest in the ultrasound image when at least a portion of the pair of calipers is placed in a region of uncertainty on the boundary. The disclosed embodiments enable the uncertainty on the boundary of the region to be characterized and to be indicated to the user so that a pair of calipers can be properly located (e.g., automatically or manually) to improve workflow and to provide better patient outcomes. In addition, the uncertainty is determined in a faster manner and more accurately.

With the preceding in mind, and by way of providing useful context, FIG. 1 depicts a high-level view of components of an ultrasound system 10 that may be employed in accordance with the present approach. The illustrated ultrasound system 10 includes a transducer array 14 having transducer elements suitable for contact with a subject or patient 18 during an imaging procedure. The transducer array 14 may be configured as a two-way transducer capable of transmitting ultrasound waves into and receiving such energy from the subject or patient 18. In such an implementation, in the transmission mode the transducer array elements convert electrical energy into ultrasound waves and transmit it into the patient 18. In reception mode, the transducer array elements convert the ultrasound energy received from the patient 18 (backscattered waves) into electrical signals.

Each transducer element is associated with respective transducer circuitry, which may be provided as one or more application specific integrated circuits (ASICs) 20, which may be present in a probe or probe handle. That is, each transducer element in the array 14 is electrically connected to a respective pulser 22, transmit/receive switch 24, pre-amplifier 26, swept gain 34, and/or analog to digital (A/D) converter 28 provided as part of or on an ASIC 20. In other implementations, this arrangement may be simplified or otherwise changed. For example, components shown in the circuitry 20 may be provided upstream or downstream of the depicted arrangement, however, the basic functionality depicted will typically still be provided for each transducer element. In the depicted example, the referenced circuit functions are conceptualized as being implemented on a single ASIC 20 (denoted by dashed line), however it may be appreciated that some or all of these functions may be provided on the same or different integrated circuits.

Also depicted in FIG. 1, a variety of other imaging components are provided to enable image formation with the ultrasound system 10. Specifically, the depicted example of an ultrasound system 10 also includes a beam former 32, a control panel 36, a receiver 38, and a scan converter 40 that cooperate with the transducer circuitry to produce an image or series of images 42 that may be stored and/or displayed to an operator or otherwise processed as discussed herein. The transducer array 14 may be communicate the ultrasound data to the beam-former via a wired connection or wireless connection (e.g., via a wireless communication unit that is part of the transducer array that communicates over a wi-fi network, utilizing Bluetooth® technique, or some other manner). A processing component 44 (e.g., a microprocessor or processing circuitry) and a memory 46 of the system 10, such as may be present control panel 36, may be used to execute stored software code, instructions, or routines for processing the acquired ultrasound signals to generate meaningful images and/or motion frames, which may be displayed on a display 47 of the ultrasound system 10. The term "code" or "software code" used herein refers to any instructions or set of instructions that control the ultrasound system 10. The code or software code may exist in a computer-executable form, such as machine code, which is the set of instructions and data directly executed by the processing component 44 of the control panel 36, human-understandable form, such as source code, which may be compiled in order to be executed by the processing component 44 of the control panel 36, or an intermediate form, such as object code, which is produced by a compiler. In some embodiments, the ultrasound system 10 may include a plurality of controllers.

As an example, the memory 46 may store processor-executable software code or instructions (e.g., firmware or software), which are tangibly stored on a non-transitory computer readable medium. Additionally or alternatively, the memory 46 may store data. As an example, the memory 46 may include a volatile memory, such as random access memory (RAM), and/or a nonvolatile memory, such as read-only memory (ROM), flash memory, a hard drive, or any other suitable optical, magnetic, or solid-state storage medium, or a combination thereof. Furthermore, processing component 44 may include multiple microprocessors, one or more "general-purpose" microprocessors, one or more special-purpose microprocessors, and/or one or more application specific integrated circuits (ASICS), or some combination thereof. For example, the processing component 44 may include one or more reduced instruction set (RISC) or complex instruction set (CISC) processors. The processing component 44 may include multiple processors, and/or the memory 46 may include multiple memory devices.

The processing component 44 may characterize uncertainty on a boundary of a region of interest. In particular, the processing component 44 may input an ultrasound image having the region of interest into a trained neural network, output from the trained neural network a first prediction of the boundary of the region of interest and a second prediction of a region segmentation of the region of interest, and determine an uncertainty on the boundary based on mismatch between the first prediction and the second prediction. In certain embodiments, the processing component 44 provides a user-perceptible indication of uncertainty when mismatch is present between the first prediction and the second prediction. This may include indicating on the ultrasound image any region of uncertainty on the boundary. In certain embodiments, the processing component 44 automatically places a pair of calipers on the region of interest in the ultrasound image in the absence of uncertainty on the boundary.

In certain embodiments, the inputted ultrasound image may include a pair of calipers placed or marked on the region of interest. In this scenario, in certain embodiments, the processing component 44 provides an alert to a user when at least a portion of the pair of calipers is placed in a region of uncertainty on the boundary. In certain embodiments, the processing component 44 provides a user-perceptible indication on the ultrasound image of any end of the pair of calipers placed in a region of uncertainty on the boundary. For example, any end of the pair of calipers in the region of uncertainty a different color from the rest of the pair of calipers. In another example, the region of uncertainty itself may be highlighted on the ultrasound image. In certain embodiments, the processing component 44 alters placement of the pair of calipers on the region of interest in the ultrasound image when at least a portion of the pair of calipers is placed in a region of uncertainty on the boundary.

Ultrasound information may be processed by other or different mode-related modules (e.g., B-mode, Color Doppler, power Doppler, M-mode, spectral Doppler anatomical M-mode, strain, strain rate, and the like) to form 2D or 3D data sets of image frames and the like. For example, one or more modules may generate B-mode, color Doppler, power Doppler, M-mode, anatomical M-mode, strain, strain rate, spectral Doppler image frames and combinations thereof, and the like. The image frames are stored and timing information indicating a time at which the image frame was acquired in memory may be recorded with each image frame. The modules may include, for example, a scan conversion module to perform scan conversion operations to convert the image frames from Polar to Cartesian coordinates. A video processor module may be provided that reads the image frames from a memory and displays the image frames in real time while a procedure is being carried out on a patient. A video processor module may store the image frames in an image memory, from which the images are read and displayed. The ultrasound system 10 shown may comprise a console system, or a portable system, such as a hand-held or laptop-type system.

The ultrasound system 10 may be operable to continuously acquire ultrasound scan data at a frame rate that is suitable for the imaging situation in question. Typical frame rates may range from 20-120 but may be lower or higher. The acquired ultrasound scan data may be displayed on the display 47 at a display-rate that can be the same as the frame rate, or slower or faster. An image buffer may be included for storing processed frames of acquired ultrasound scan data that are not scheduled to be displayed immediately. Preferably, the image buffer is of sufficient capacity to store at least several minutes worth of frames of ultrasound scan data. The frames of ultrasound scan data are stored in a manner to facilitate retrieval thereof according to its order or time of acquisition. The image buffer may be embodied as any known data storage medium.

The display 47 may be any device capable of communicating visual information to a user. For example, the display 47 may include a liquid crystal display, a light emitting diode display, and/or any suitable display or displays. The display 47 can be operable to present ultrasound images and/or any suitable information.

Components of the ultrasound system 10 may be implemented in software, hardware, firmware, and/or the like. The various components of the ultrasound system 10 may be communicatively linked. Components of the ultrasound may be implemented separately and/or integrated in various forms.

Figure 2:
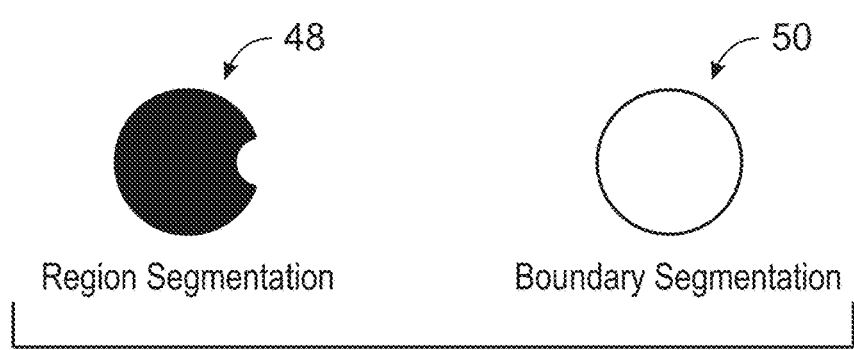
FIG. 2 is a schematic diagram of an example of a first type of disagreement between region segmentation and boundary segmentation in predicting a boundary of a region of interest.
Figure 3:
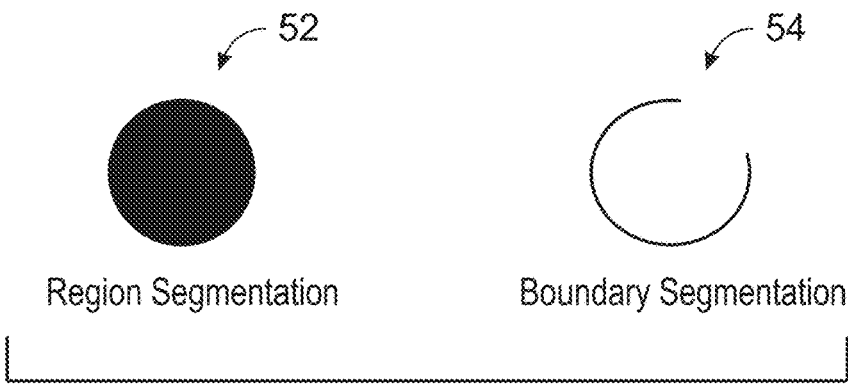
FIG. 3 is a schematic diagram an example of a second type of disagreement between region segmentation and boundary segmentation in predicting a boundary of a region of interest.

For caliper placements, a boundary of a region of interest can be predicted in two (e.g., supplementary and independent) ways. In the first way, region segmentation of the region of interest is performed and then followed by boundary extraction. The first way is texture driven. In the second way, direct boundary prediction (e.g., boundary segmentation prediction) is utilized. The second way is gradient driven. In case of agreement between the first way and the second way, there exists no uncertainty in boundary predictions. However, uncertainty exists when the first way and the second way have disagreements. These disagreements can manifest in different ways. As depicted in FIG. 2, the region segmentation (i.e., the first way) under segments as indicated by reference numeral 48, while the direct boundary segmentation prediction (i.e., the second way) predicts the full boundary (e.g., boundary segmentation) as indicated by reference numeral 50. As depicted in FIG. 3, the region segmentation (i.e., the first way) predicts or segments the full region of interest as indicated reference numeral 52, while the direct boundary segmentation prediction under segments the boundary of the region of interest as indicated by reference numeral 54.

Figure 4:
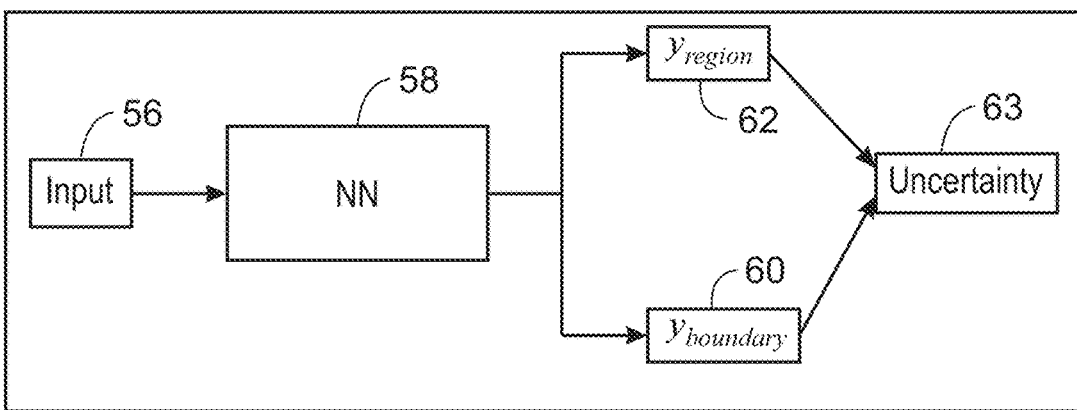
FIG. 4 is a schematic diagram illustrating how uncertainty on a boundary of a region of interest in an image is characterized, in accordance with aspects of the present disclosure.

FIG. 4 is a schematic diagram illustrating how uncertainty on a boundary of a region of interest in an image is characterized. As depicted in FIG. 4, an input 56 is provided to or inputted into a trained neural network 58 (e.g., deep learning-based neural network). The input 56 is an image (e.g., ultrasound image) having a region of interest (e.g., vaginal area). In certain embodiments, the ultrasound image includes a pair of calipers placed or marked on the region of interest. In certain embodiments, the ultrasound image does not have a pair of calipers placed or marked on the region of interest. The trained neural network 58 is configured to output a prediction of a boundary of the region of interest in the ultrasound image (i.e., boundary segmentation prediction 60, $y_{boundary}$) utilizing a boundary segmentation model. The trained neural network 58 utilizes unsigned distance map for the boundary segmentation prediction 60. The trained neural network 58 is also configured to output a prediction of region segmentation of the region of interest in the ultrasound image (i.e., region segmentation prediction 62, $y_{region}$) utilizing a region segmentation model. The trained neural network 58 utilized conventional Dice loss for the region segmentation prediction 62. The trained neural network 58 is trained to infer the disagreement (e.g., mismatch) between the boundary segmentation prediction 60 and the region segmentation prediction 62. This disagreement enables an uncertainty 63 (e.g., boundary uncertainty) to be determined on the boundary based on the uncertainty 63 between the boundary segmentation prediction 60 and the region segmentation prediction 62 by comparing the boundary prediction 60 and the region segmentation prediction 62. In particular, the margins estimated by the boundary segmentation prediction 60 and an edge of the region segmentation prediction 62 are analyzed. In certain embodiments, the determination of the uncertainty 63 is done via postprocessing. In certain embodiments, the determination of the uncertainty 63 is done by another trained neural network or the same trained neural network 58. This uncertainty 63 can be determined with a single pass through the process described in FIG. 4.

Figure 5:
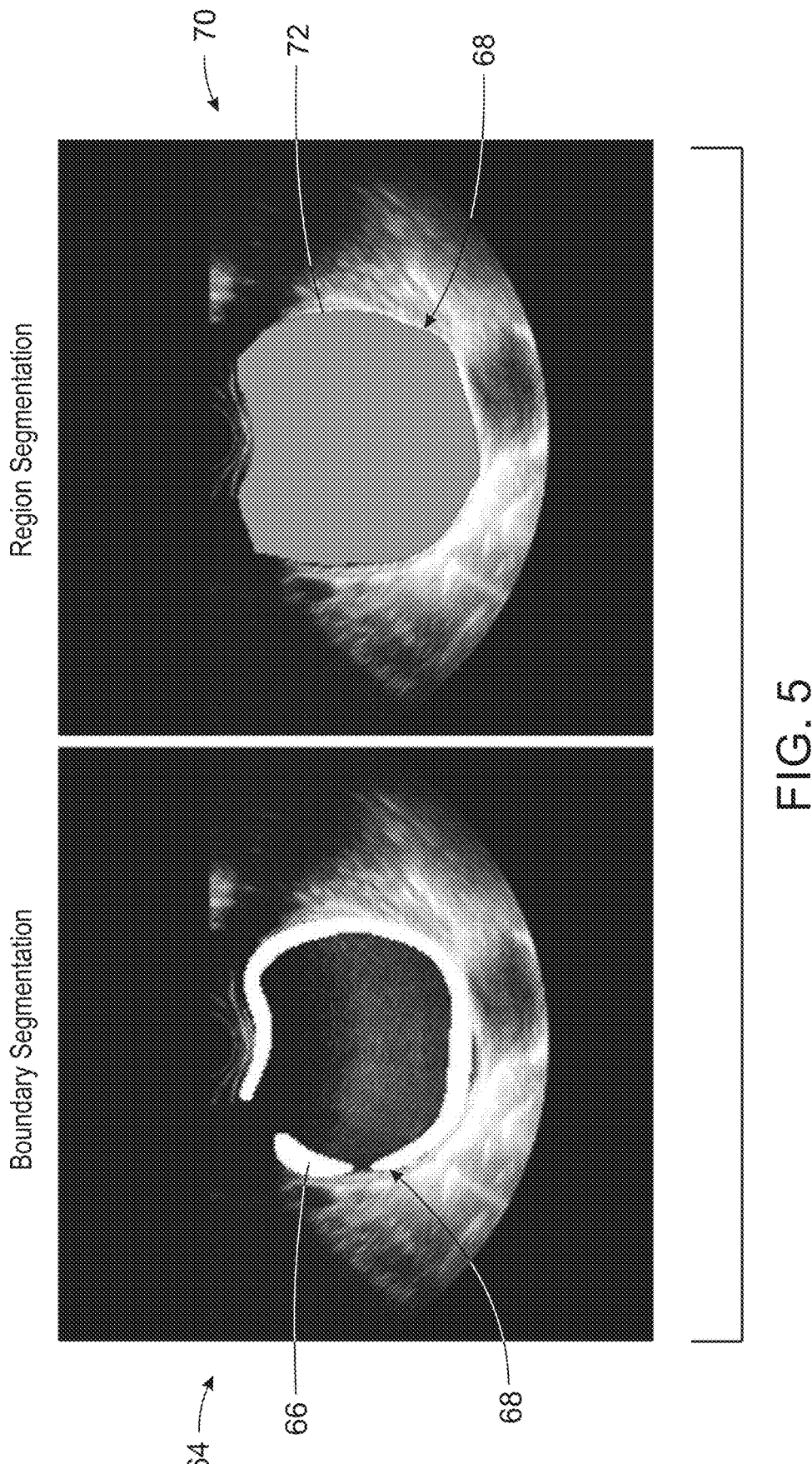
FIG. 5 is an example of an ultrasound image with a boundary segmentation mask and the same ultrasound image with a region segmentation mask (e.g., with boundary uncertainty), in accordance with aspects of the present disclosure.

The boundary segmentation prediction 60 and the region segmentation prediction 62 reinforce each other at locations with high certainty along the margin. Also, locations along the margin where the boundary segmentation prediction 60 and the region segmentation prediction 62 lack reinforcement are deemed uncertain. FIG. 5 is an example of an ultrasound image with a boundary segmentation mask and the same ultrasound image with a region segmentation mask (e.g., with boundary uncertainty). The ultrasound image in FIG. 5 is derived from a trans-vaginal ultrasound scan. Image 64 is an ultrasound image with a boundary segmentation mask 66 as predicted by the trained neural network 58 in FIG. 4 overlaid on a region of interest 68. Image 70 is the same ultrasound image with a region segmentation mask 72 as predicted by the trained neural network 58 in FIG. 4 overlaid on the region of interest 68. There is uncertainty in the boundary of the region of interest 68 between the boundary segmentation in the image 64 and the region segmentation in the image 70. In particular, the boundary in the boundary segmentation in image 64 is under segmented.

Figure 6:
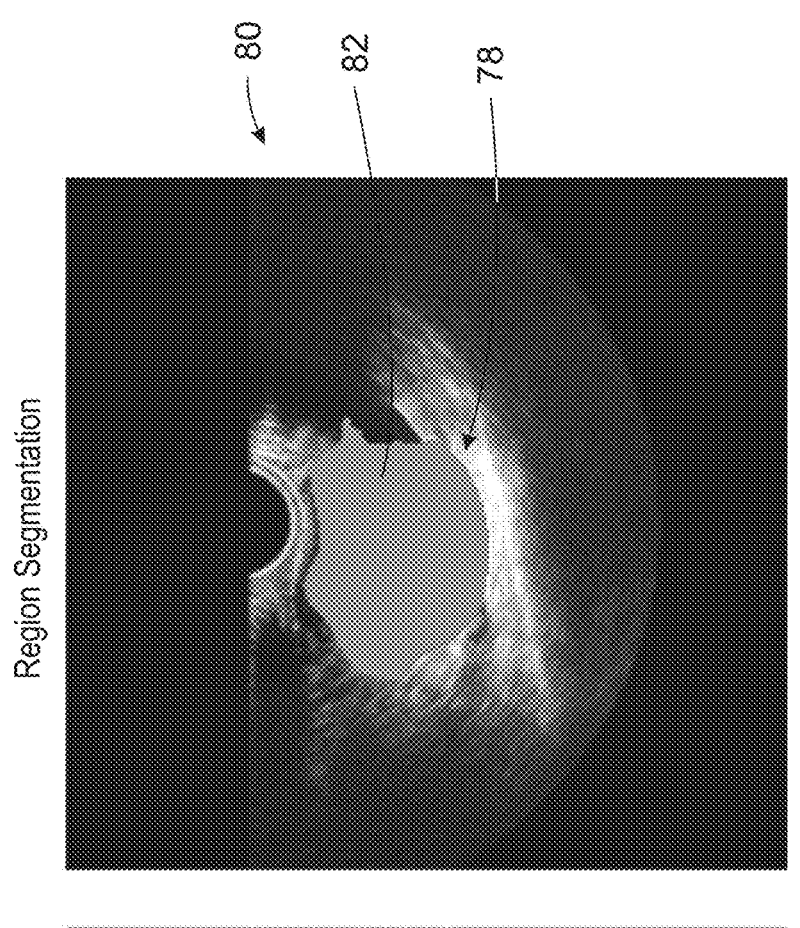
FIG. 6 is another example of an ultrasound image with a boundary segmentation mask and the same ultrasound image with a region segmentation mask (e.g., with boundary uncertainty), in accordance with aspects of the present disclosure.
Figure 6:
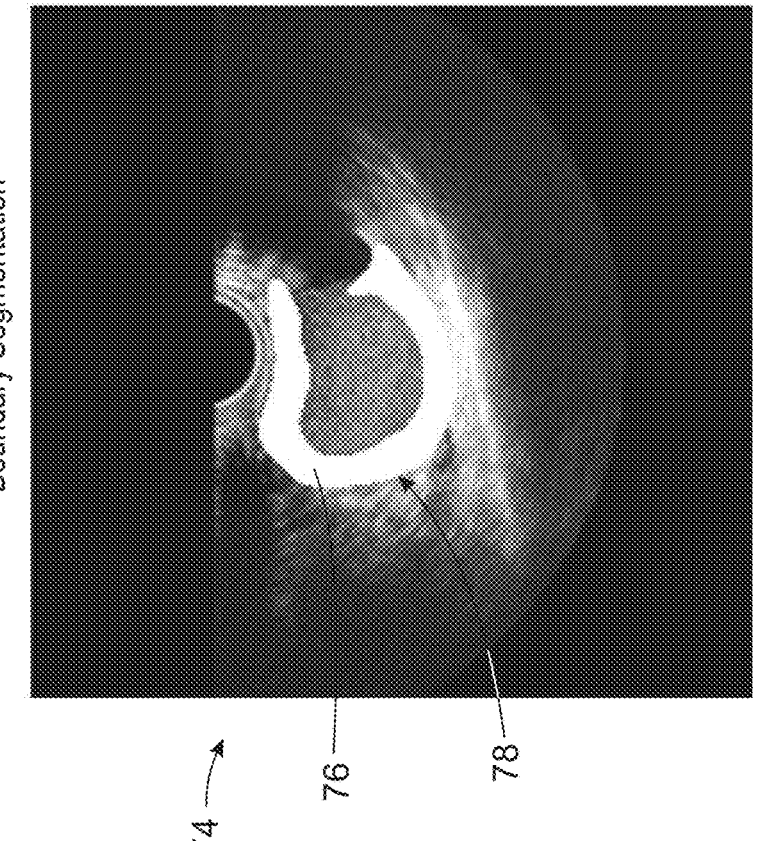

FIG. 6 is another example of an ultrasound image with a boundary segmentation mask and the same ultrasound image with a region segmentation mask (e.g., with boundary uncertainty). The ultrasound image in FIG. 6 is derived from a trans-vaginal ultrasound scan. Image 74 is an ultrasound image with a boundary segmentation mask 76 as predicted by the trained neural network 58 in FIG. 4 overlaid on a region of interest 78. Image 80 is the same ultrasound image with a region segmentation mask 82 as predicted by the trained neural network 58 in FIG. 4 overlaid on the region of interest 78. There is uncertainty in the boundary of the region of interest 78 between the boundary segmentation in the image 74 and the region segmentation in the image 80. In particular, the boundary in the boundary segmentation in image 74 is under segmented.

Figure 7:
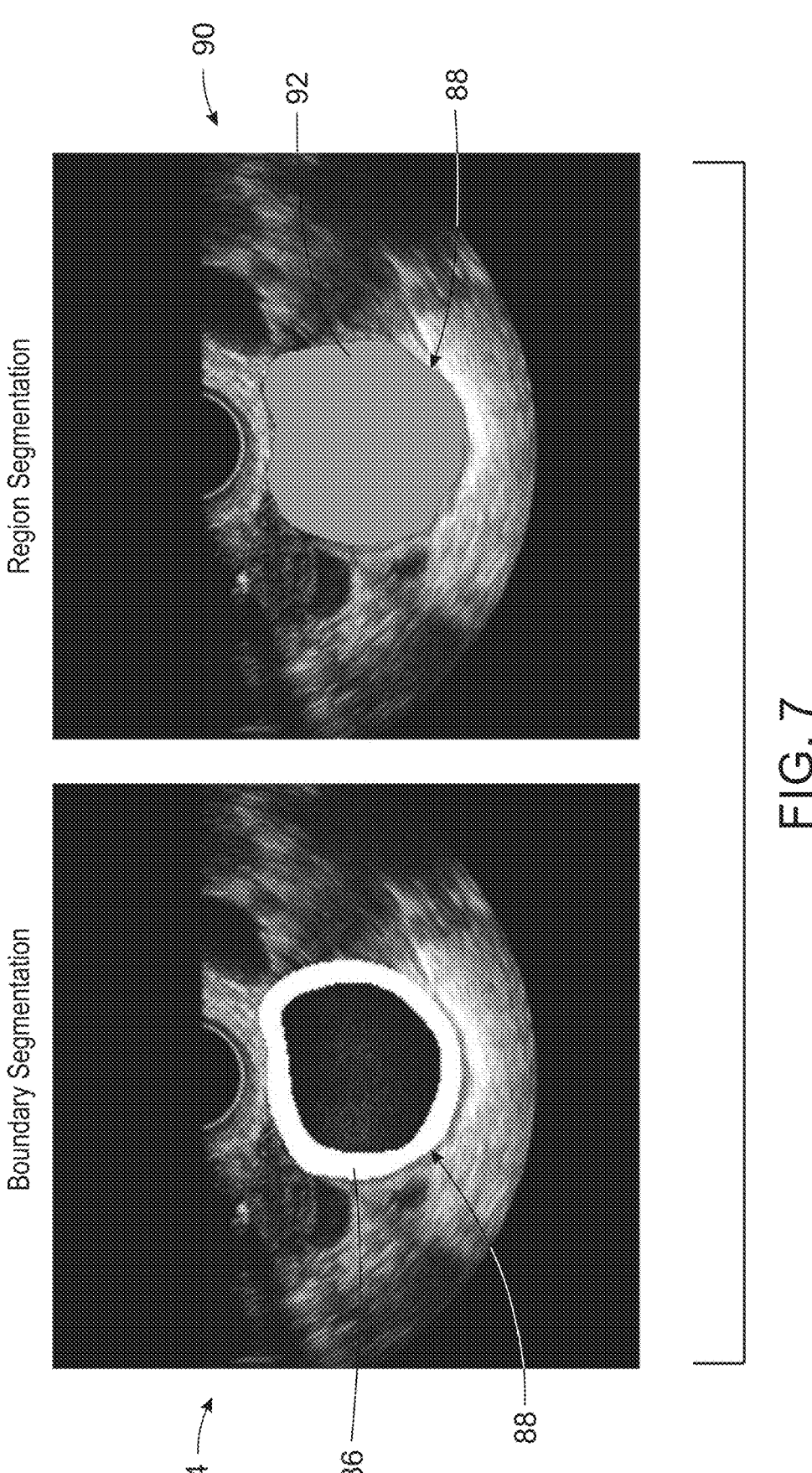
FIG. 7 is an example of an ultrasound image with a boundary segmentation mask and the same ultrasound image with a region segmentation mask (e.g., with a highly certain boundary), in accordance with aspects of the present disclosure.

FIG. 7 is an example of an ultrasound image with a boundary segmentation mask and the same ultrasound image with a region segmentation mask (e.g., with a highly certain boundary). The ultrasound image in FIG. 7 is derived from a trans-vaginal ultrasound scan. Image 84 is an ultrasound image with a boundary segmentation mask 86 as predicted by the trained neural network 58 in FIG. 4 overlaid on a region of interest 88. Image 90 is the same ultrasound image with a region segmentation mask 92 as predicted by the trained neural network 58 in FIG. 4 overlaid on the region of interest 88. There is high certainty in the boundary of the region of interest 88 between the boundary segmentation in the image 84 and the region segmentation in the image 90 as shown by the well-defined boundary features in both the images 84 and 90.

Figure 8:
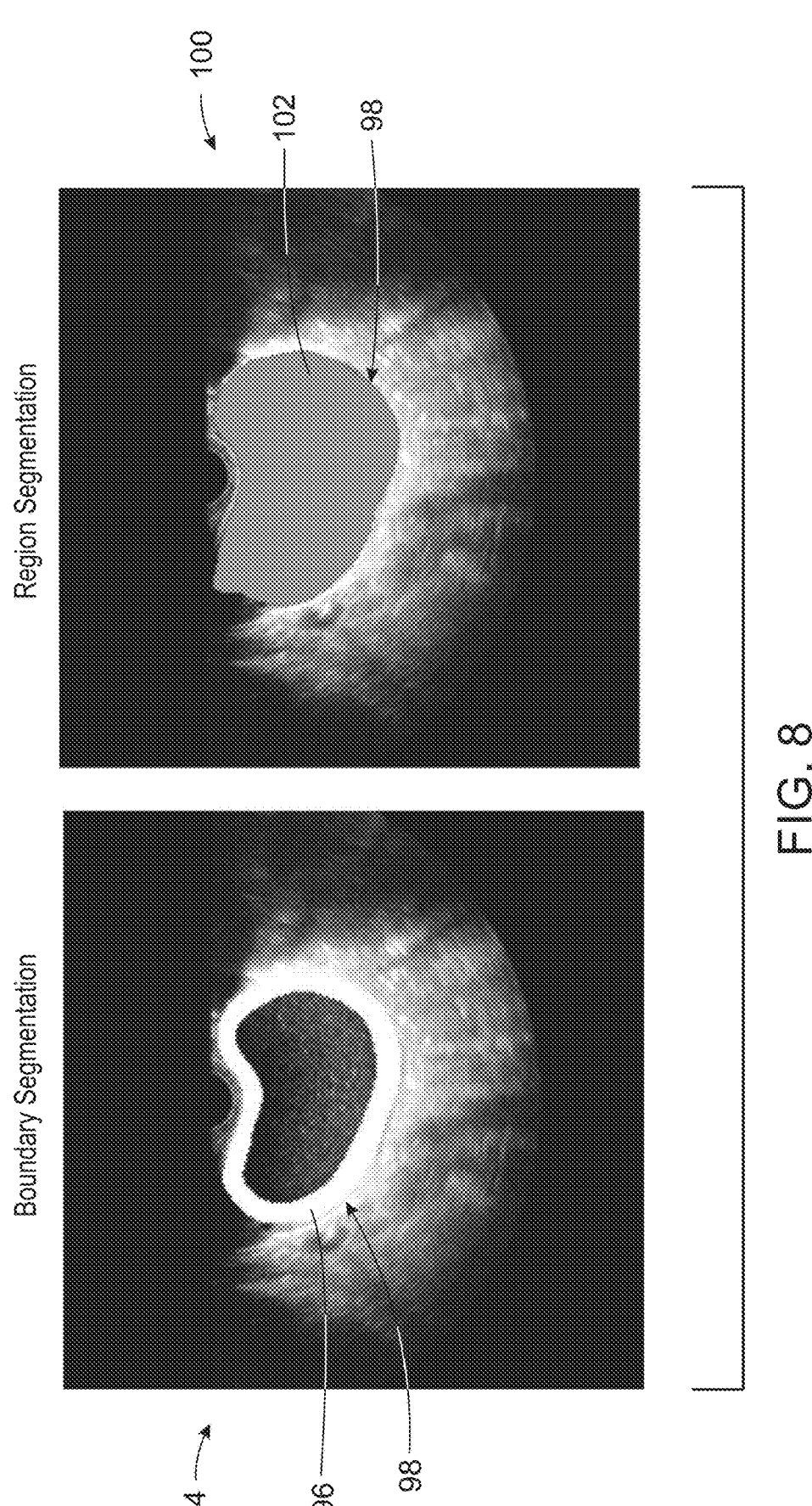
FIG. 8 is another example of an ultrasound image with a boundary segmentation mask and the same ultrasound image with a region segmentation mask (e.g., with a highly certain boundary), in accordance with aspects of the present disclosure.

FIG. 8 is another example of an ultrasound image with a boundary segmentation mask and the same ultrasound image with a region segmentation mask (e.g., with a highly certain boundary). The ultrasound image in FIG. 8 is derived from a trans-vaginal ultrasound scan. Image 94 is an ultrasound image with a boundary segmentation mask 96 as predicted by the trained neural network 58 in FIG. 4 overlaid on a region of interest 98. Image 100 is the same ultrasound image with a region segmentation mask 102 as predicted by the trained neural network 58 in FIG. 4 overlaid on the region of interest 98. There is high certainty in the boundary of the region of interest 98 between the boundary segmentation in the image 94 and the region segmentation in the image 100 as shown by the well-defined boundary features in both the images 94 and 100.

Figure 9:
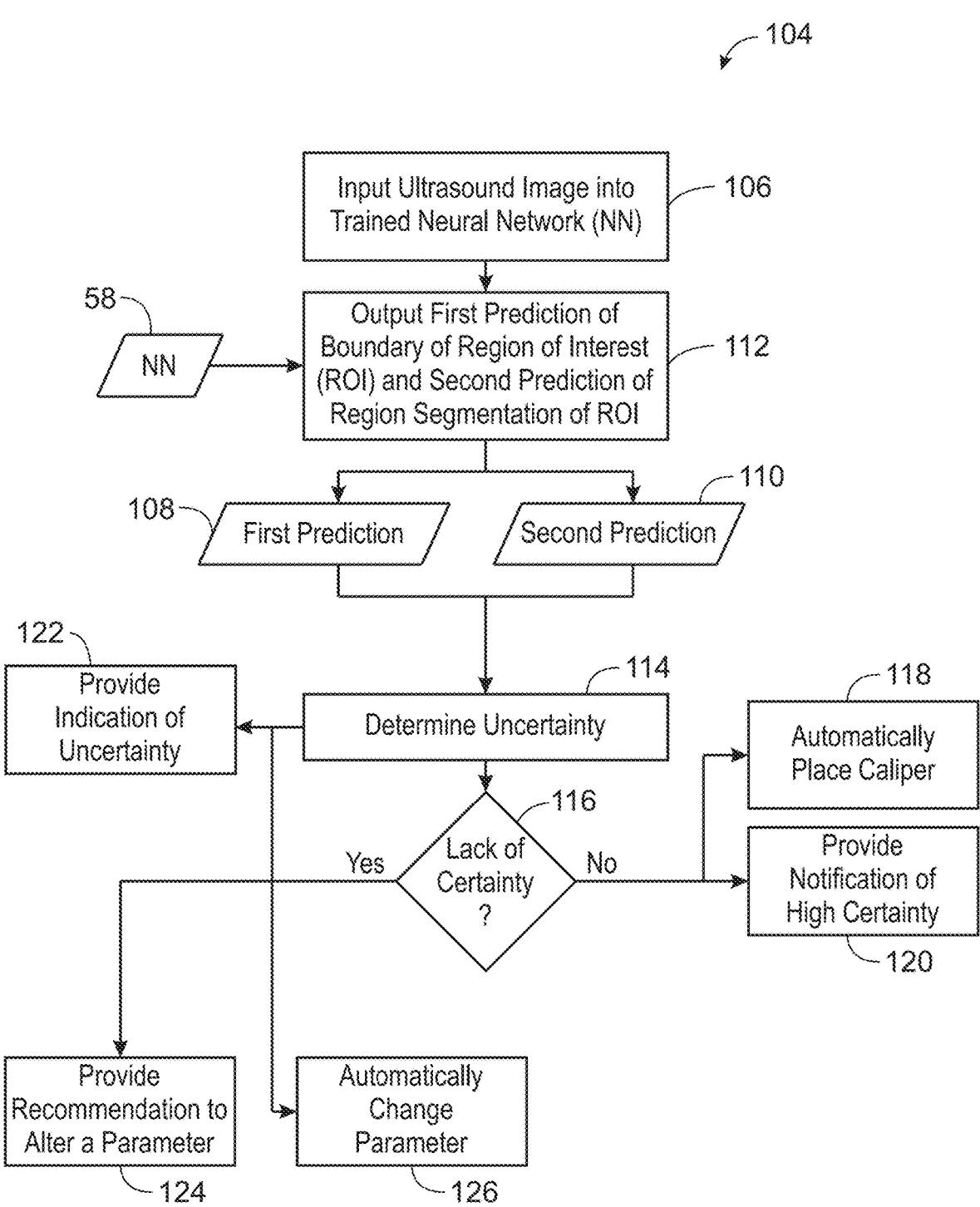
FIG. 9 is a flow chart of a method for characterizing uncertainty on a boundary of a region of interest (e.g., where ultrasound image is not marked with a pair of calipers), in accordance with aspects of the presence disclosure.

FIG. 9 is a flow chart of a method 104 for characterizing uncertainty on a boundary of a region of interest (e.g., where ultrasound image is not marked with a pair of calipers). One or more steps of the method 104 may be performed by processing circuitry of the ultrasound system 10 in FIG. 1 or a remote computing system. One or more steps of the method 104 may be performed simultaneously and/or in a different order shown in FIG. 9. It should be noted that besides ultrasound images, the method 104 may apply to medical images acquired with other types of imaging modalities (e.g., magnetic resonance imaging (MRI), nuclear medicine (NM) imaging, computed tomography (CT) imaging, conventional X-ray imaging, etc.).

The method 104 includes inputting an ultrasound image having the region of interest (e.g., not marked with a pair of calipers) into the trained neural network 58 (e.g., as described in FIG. 4) (block 106). The method 104 also includes outputting from the trained neural network 58 a first prediction 108 of the boundary of the region of interest (e.g., $y_{boundary}$ 60 in FIG. 4) and a second prediction 110 of a region segmentation of the region of interest (e.g., $y_{region}$ 62 in FIG. 4) (block 112). The method 104 further includes determining an uncertainty (e.g., boundary uncertainty) on the boundary based on mismatch between the first prediction 108 of the boundary of the region of interest and the second prediction 110 of the region segmentation of the region of interest by comparing the first prediction 108 and the second prediction 110 (block 114). Any disagreement between the first prediction 108 of the boundary of the region of interest and the second prediction 110 of the region segmentation of the region of interest enables an uncertainty to be determined on the boundary based on mismatch between the first prediction 108 of the boundary of the region of interest and second prediction 110 of the region segmentation of the region of interest. In particular, the margins estimated by the first prediction 108 of the boundary of the region of interest and the second prediction 110 of the region segmentation of the region of interest are analyzed. In certain embodiments, the determination of the uncertainty is done via post-processing. In certain embodiments, the determination of the uncertainty is done by another trained neural network or the same trained neural network 58.

The method 104 includes based on the determined uncertainty determining if there is a lack of certainty (block 116). In certain embodiments, if there is not a lack of certainty, the method 104 includes automatically placing a pair of calipers on the region of interest in the ultrasound image (block 118). In certain embodiments, the user can overrule the automatic placement of the pair of calipers. In certain embodiments, if there is not a lack of certainty, the method 104 includes providing a notification (e.g., textual notification on display or ultrasound image) that the boundary of the region of interest is highly certain and/or that a pair of calipers can be placed (block 120).

In certain embodiments, if there is a lack of certainty, the method 104 includes providing a user-perceptible indication of the uncertainty (block 122). In certain embodiments, the user-perceptible indication includes indicating on the ultrasound image any region of uncertainty on the boundary. In certain embodiments, the user-perceptible indication may be an indicator or mark identifying the region of uncertainty (which may or may not be accompanied by text indicating the region of uncertainty). In certain embodiments, the user-perceptible indication may be highlighting the region of uncertainty. In certain embodiments, if there is a lack of uncertainty, the method 104 includes providing a recommendation to alter a parameter of one of segmentation models (e.g., boundary segmentation model or region segmentation model) and to input the ultrasound image into the trained neural network 58 again (block 124). For example, a filter parameter (e.g., gradient filter) may be altered for the boundary segmentation model. In certain embodiments, if there is a lack of uncertainty, the method 104 includes automatically altering a parameter of one of segmentation models (e.g., boundary segmentation model or region segmentation model) and inputting the ultrasound image into the trained neural network 58 again (block 126). A notice may or may be provided to the user if a parameter was automatically altered and the ultrasound image was inputted into the trained neural network 58 again.

Figure 10:
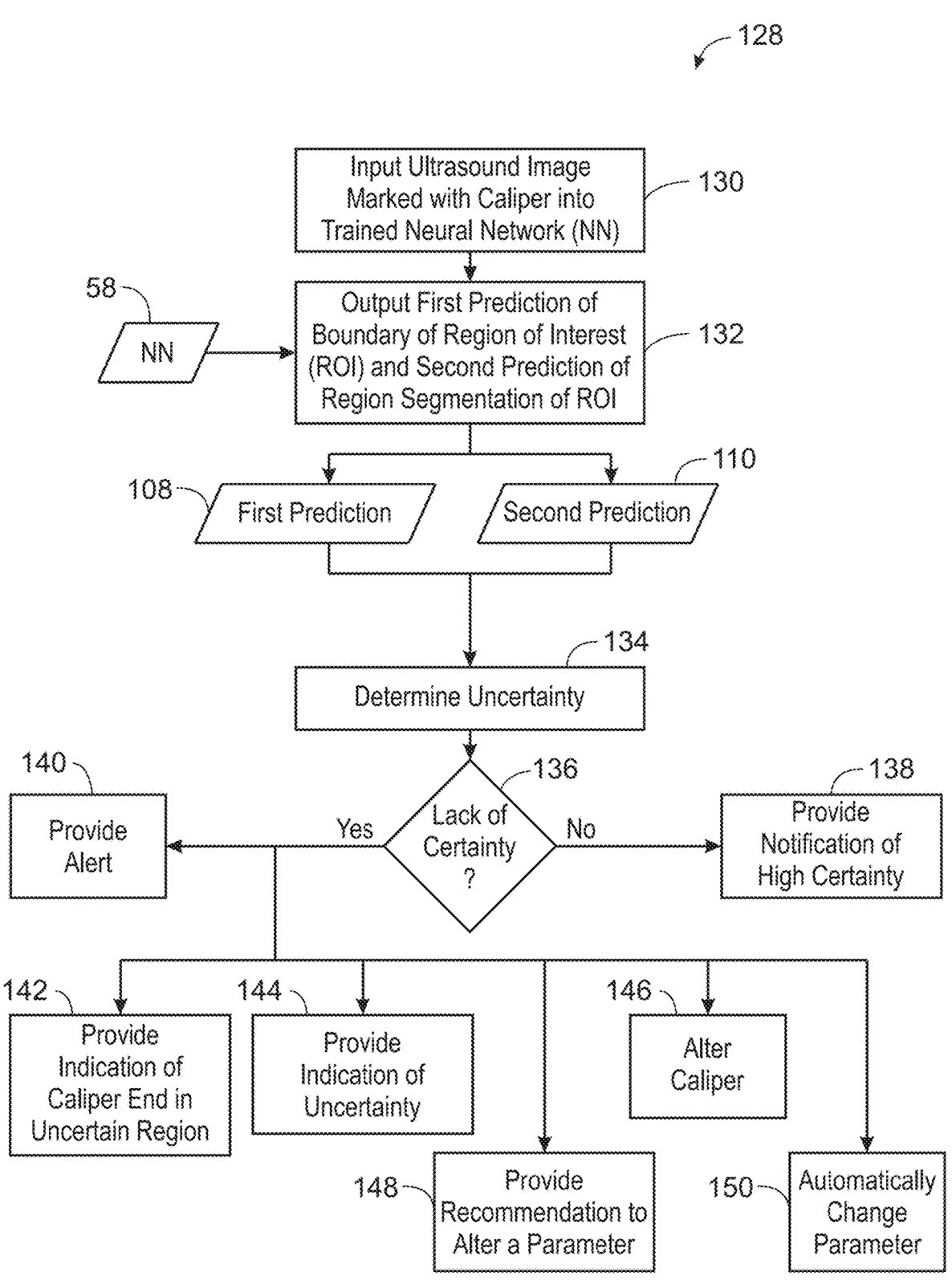
FIG. 10 is a flow chart of a method for characterizing uncertainty on a boundary of a region of interest (e.g., where a pair of calipers is placed on the ultrasound image), in accordance with aspects of the presence disclosure.

FIG. 10 is a flow chart of a method 128 for characterizing uncertainty on a boundary of a region of interest (e.g., where a pair of calipers is placed on the ultrasound image) One or more steps of the method 128 may be performed by processing circuitry of the ultrasound system 10 in FIG. 1 or a remote computing system. One or more steps of the method 128 may be performed simultaneously and/or in a different order shown in FIG. 10. It should be noted that besides ultrasound images, the method 128 may apply to medical images acquired with other types of imaging modalities (e.g., magnetic resonance imaging (MRI), nuclear medicine (NM) imaging, computed tomography (CT) imaging, conventional X-ray imaging, etc.).

The method 128 includes inputting an ultrasound image having the region of interest (e.g., marked with a pair of calipers) into the trained neural network 58 (e.g., as described in FIG. 4) (block 130). The method 128 also includes outputting from the trained neural network 58 a first prediction of the boundary of the region of interest 108 (e.g., $y_{boundary}$ 60 in FIG. 4) and a second prediction of a region segmentation of the region of interest 110 (e.g., $y_{region}$ 62 in FIG. 4) (block 132). The method 128 further includes determining an uncertainty (e.g., boundary uncertainty) on the boundary based on mismatch between the first prediction 108 and the second prediction 110 by comparing the first prediction 108 and the second prediction 110 (block 134). Any disagreement between the first prediction 108 and the second prediction 110 enables an uncertainty on the boundary to be determined based on mismatch between the first prediction 108 and second prediction 110. In particular, the margins estimated by the first prediction 108 and the second prediction 110 are analyzed. In certain embodiments, the determination of the uncertainty is done via post-processing.

In certain embodiments, the determination of the uncertainty is done by another trained neural network or the same trained neural network 58.

The method 128 includes based on the determined uncertainty determining if there is a lack of certainty (block 136). In certain embodiments, if there is not a lack of certainty, the method 104 includes providing a notification that the boundary of the region of interest is highly certain and/or that a pair of calipers can be placed (block 138). In certain embodiments, if there is not a lack of certainty, no notification may be provided and the user may proceed.

In certain embodiments, if there is a lack of certainty, the method 128 includes providing an alert to a user when at least a portion of the pair of calipers is placed in a region of uncertainty on the boundary (block 140). In certain embodiments, if there is a lack of certainty, the method 104 includes providing a user-perceptible indication on the ultrasound image of any end of the pair of calipers placed in a region of uncertainty on the boundary (block 142). In certain embodiments, the user-perceptible indication includes having any end of the pair of calipers in the region of uncertainty shown in a different color from the rest of the pair of calipers. For example, if the pair of calipers is colored yellow, an end in a region of uncertainty may be colored red. In certain embodiments, if there is a lack of certainty, the method 104 includes providing a user-perceptible indication of the uncertainty (block 144). In certain embodiments, the user-perceptible indication may be an indicator or mark identifying the region of uncertainty (which may or may not be accompanied by text indicating the region of uncertainty). In certain embodiments, the user-perceptible indication may be highlighting the region of uncertainty. In certain embodiments, if there is a lack of certainty, the method 128 includes altering placement of the pair of calipers on the region of interest in the ultrasound image when at least a portion of the pair of calipers is placed in a region of uncertainty between on the boundary (block 146). In certain embodiments, the user can overrule the automatic placement of the pair of calipers.

In certain embodiments, if there is a lack of uncertainty, the method 128 includes providing a recommendation to alter a parameter of one of segmentation models (e.g., boundary segmentation model or region segmentation model) and to input the ultrasound image into the trained neural network 58 again (block 148). For example, a filter parameter (e.g., gradient filter) may be altered for the boundary segmentation model. In certain embodiments, if there is a lack of uncertainty, the method 128 includes automatically altering a parameter of one of segmentation models (e.g., boundary segmentation model or region segmentation model) and inputting the ultrasound image into the trained neural network 58 again (block 150). A notice may or may be provided to the user if a parameter was automatically altered and the ultrasound image was inputted into the trained neural network 58 again.

Figure 11:
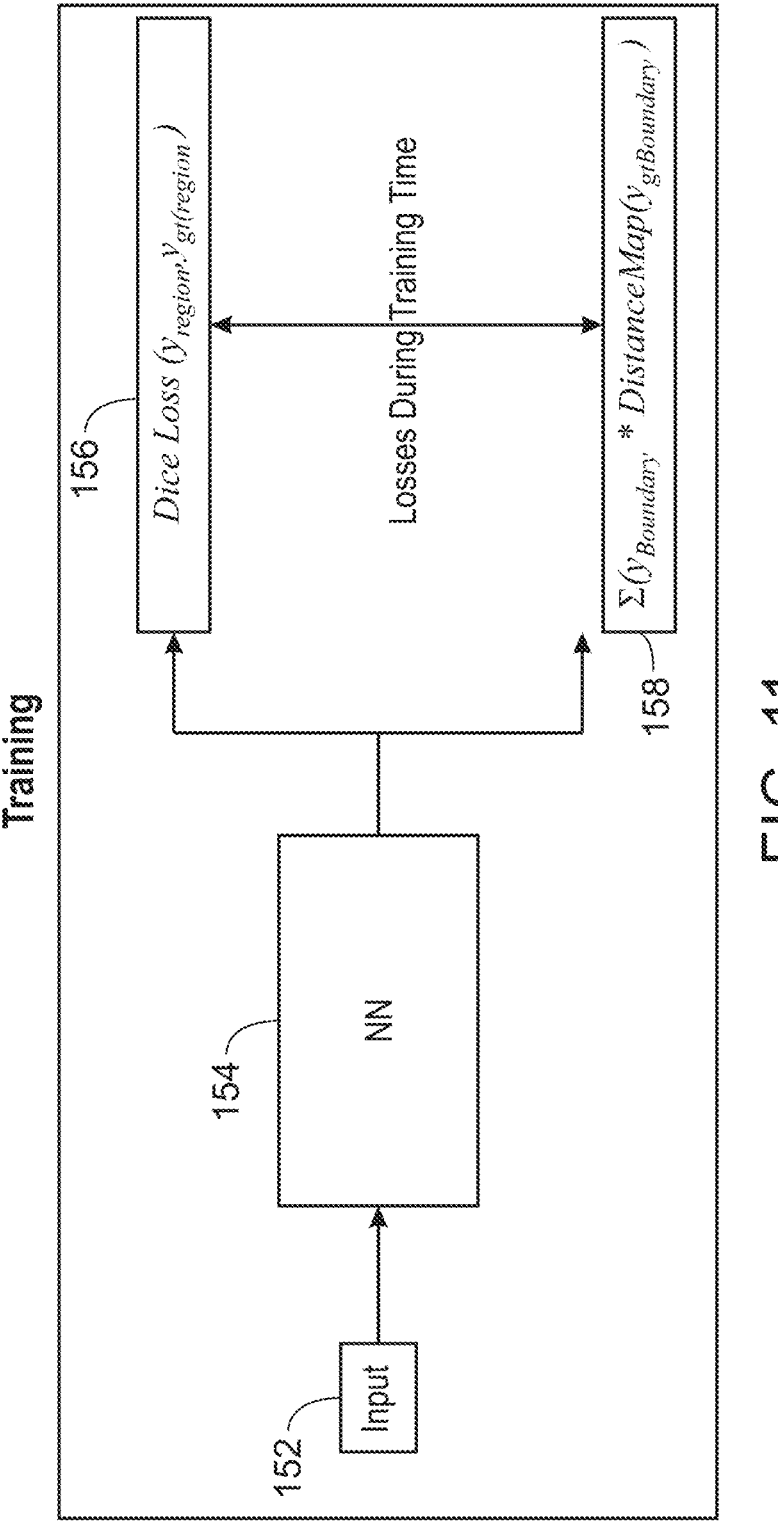
FIG. 11 is a schematic diagram illustrating training a neural network for characterizing uncertainty on a boundary of a region of interest of an image, in accordance with aspects of the present disclosure.

FIG. 11 is a schematic diagram illustrating training a neural network for characterizing uncertainty on a boundary of a region of interest of an image. As depicted in FIG. 4, an input 152 is provided to or inputted into a neural network 154. The input 152 includes input-output data pairs. In particular, the input 152 includes image pairs consisting of a borderline segmentation prediction of a region of interest in an image ($y_{boundary}$) and a ground truth of the borderline segmentation of the region of interest in the image ($y_{gtBoundary}$). The input 152 also includes image pairs consisting of a region segmentation prediction of a region of interest in an image ($y_{region}$) and a ground truth of the region segmentation of the region of interest in the image ($y_{gt(region)}$). The neural network 154 is trained utilizing supervised learning. The neural network 154 is trained on the Dice loss 156 between $y_{region}$ and $y_{gt(region)}$. The neural network 154 is also trained on the following loss function 158 between $y_{boundary}$ and $y_{gtBoundary}$:

$$\sum (y_{boundary} * \text{Distance Map} (y_{gtBoundary})). \quad (1)$$

The loss function 158 tends to 0 when the boundary is predicted accurately. The loss function 158 is negative when the predicted boundary is located inside the ground truth and positive when the predicted boundary is located outside the ground truth. The neural network 154 is trained to determine boundary uncertainty based on the comparison between the Dice loss 156 and the loss function 158 (equation 1 above). The neural network 154 is trained to become the trained neural network 58 described in FIG. 4. As mentioned above, the trained neural network 58 is trained to infer the disagreement between the boundary segmentation prediction and the region segmentation prediction. This disagreement enables an uncertainty (e.g., boundary uncertainty) to be determined based on mismatch between the boundary segmentation prediction and the region segmentation prediction by comparing the boundary segmentation prediction and the region segmentation prediction.

Figure 12:
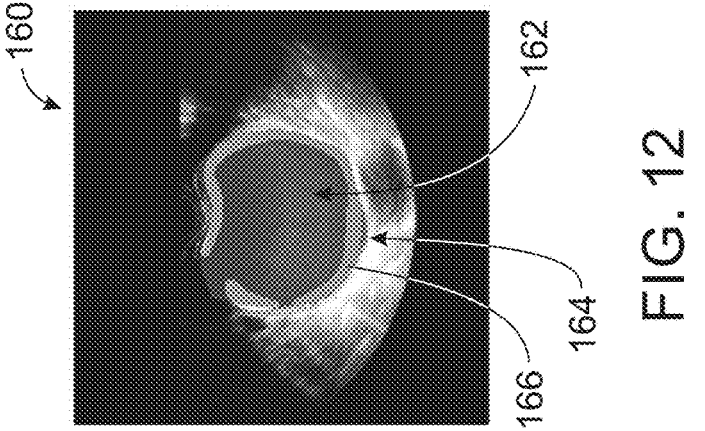
FIG. 12 is an example of a boundary predicted from a boundary segmentation overlaid on a predicted segmented region of a region of interest in an image, in accordance with aspects of the present disclosure.

FIGS. 12-15 provide examples of boundary and region segmentation predictions and characterization of their uncertainty (e.g., boundary uncertainty). The predictions (e.g., utilizing the trained neural network 58 in FIG. 4) and uncertainty characterization were conducted as described in the method 104 described above in FIG. 9. FIG. 12 is an example of a boundary predicted from a boundary segmentation overlaid on a predicted segmented region of a region of interest in an image 160 (e.g., ultrasound image). As depicted in FIG. 12, the image 160 includes a region segmentation mask 162 predicted (via the neural network 58) for a region of interest 164 (and overlaid over the region of interest 164) and a boundary segmentation mask 166 predicted (via the neural network 58) for the region of interest 164 (and overlaid over the region segmentation mask 162). As depicted in the image 160, the boundary as indicated by the boundary segmentation mask 166 is under-segmented, while the region segmentation (as indicated by the region segmentation mask 162) has been able to identify texture belonging to the region of interest 164.

Figure 13:
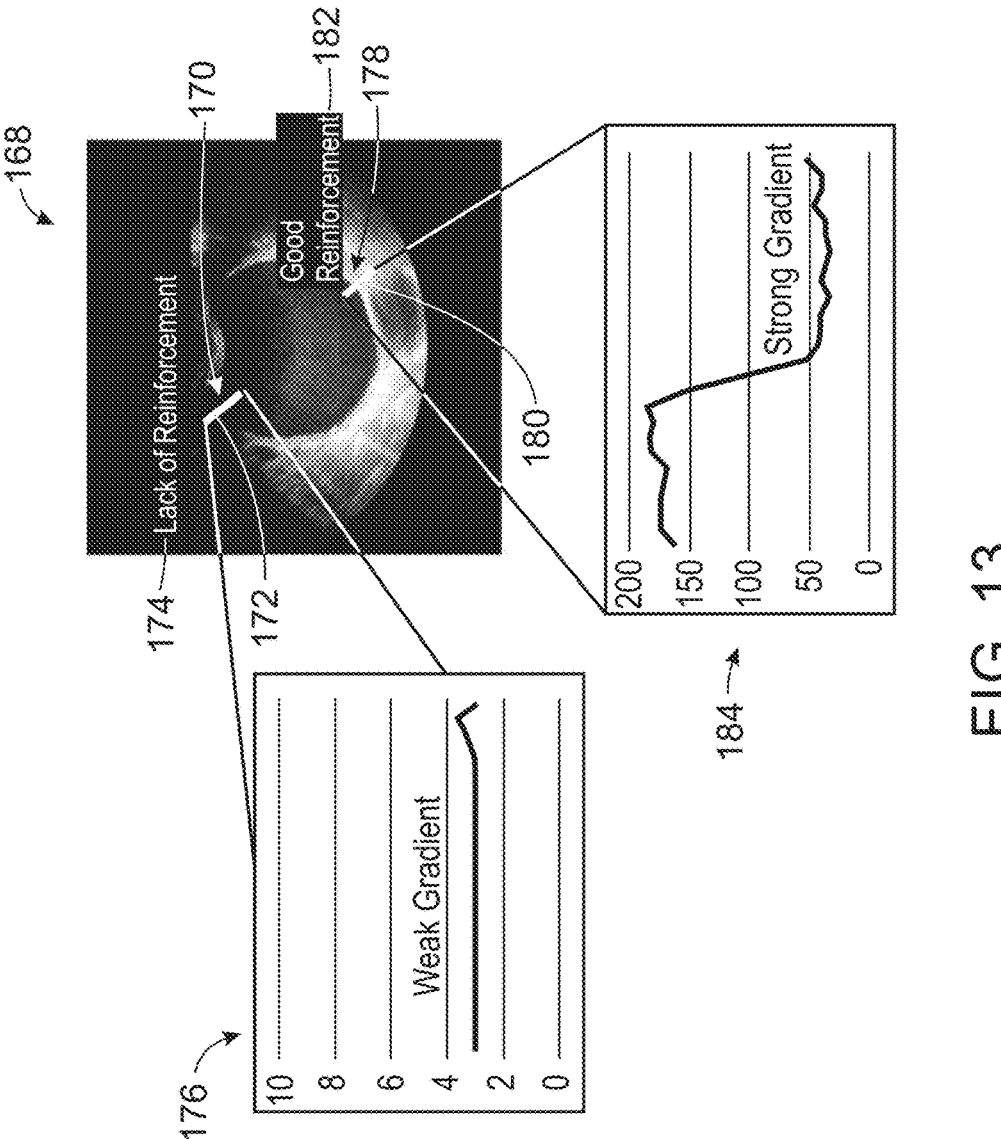
FIG. 13 is an example of a characterization of an uncertainty utilizing the predictions in FIG. 12, in accordance with aspects of the present disclosure.

FIG. 13 is an example of a characterization of an uncertainty utilizing the predictions in FIG. 12. Image 168 is derived from the same ultrasound image that image 160 is derived from. As depicted in the image 168, a region 170 with a lack of reinforcement between the boundary segmentation prediction and the region segmentation prediction is indicated by marker 172. In addition, text 174 accompanies the marker 172 to indicate the lack of reinforcement. The lack of reinforcement in the region 170 is indicated by a graph 176 representative of the intensity gradient profile in the region 170. As indicated by the graph 176, the boundary is under-segmented due to a lack of image gradient support. As depicted in the image 168, a region 178 with good reinforcement between the boundary segmentation prediction and the region segmentation prediction is indicated by the marker 180. In addition, text 182 accompanies the marker 180 to indicate the good reinforcement. The good reinforcement in the region 178 is indicated by the graph 184 representative of the intensity gradient profile in the region 178.

In certain embodiments, makers, accompanying text, and graphs may be provided for regions of the segmentation predictions that are characterized for uncertainty (e.g., boundary uncertainty) for a given image. In certain embodiments, only markers and accompanying text may be provided for regions of the segmentation predictions that are characterized for uncertainty for a given image. In certain embodiments, markers and accompanying text, and graphs are provided only for regions with a lack of reinforcement. In certain embodiments, only markers and accompanying text are provided for regions with a lack of reinforcement.

Figures 14, 15:
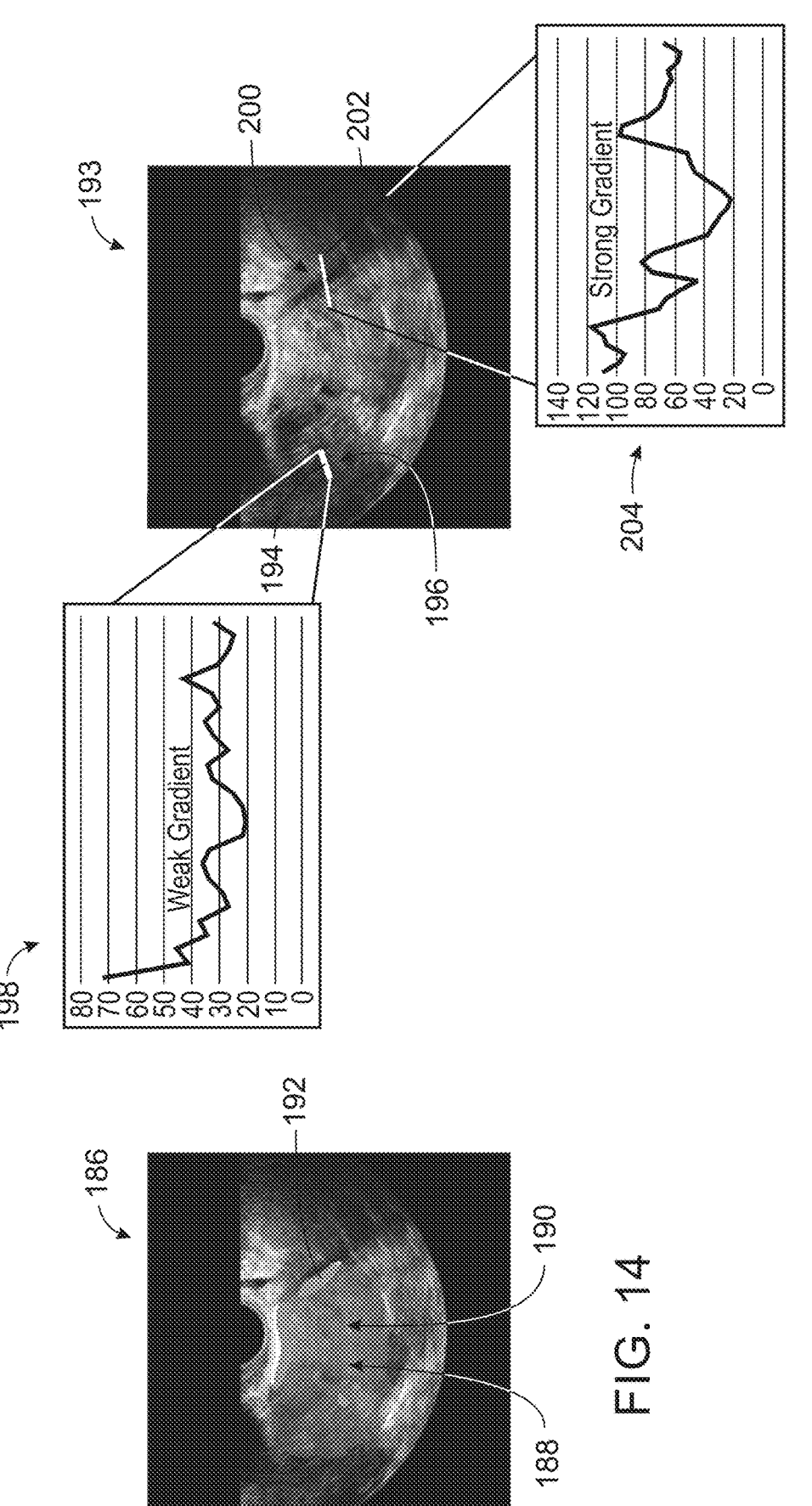
FIG. 14 is another example of a boundary predicted from a boundary segmentation overlaid on a predicted segmented region of a region of interest in an image, in accordance with aspects of the present disclosure.
FIG. 15 is an example of a characterization of an uncertainty utilizing the predictions in FIG. 14, in accordance with aspects of the present disclosure.

FIG. 14 is another example of a boundary predicted from a boundary segmentation overlaid on a predicted segmented region of a region of interest in an image 186 (e.g., ultrasound image). As depicted in FIG. 14, the image 186 includes a region segmentation mask 188 predicted (via the neural network 58) for a region of interest 190 (and overlaid over the region of interest 190) and a boundary segmentation mask 192 predicted (via the neural network 58) for the region of interest 190 (and overlaid over the region segmentation mask 164). As depicted in the image 186, the boundary as indicated by the boundary segmentation mask 192 is under-segmented, while the region segmentation (as indicated by the region segmentation mask 188) has been able to identify texture belonging to the region of interest 190.

FIG. 15 is an example of a characterization of an uncertainty utilizing the predictions in FIG. 14. Image 193 is derived from the same ultrasound image that image 186 is derived from. As depicted in the image 193, a region 194 with a lack of reinforcement between the boundary segmentation prediction and the region segmentation prediction is indicated by marker 196. The lack of reinforcement in the region 194 is indicated by a graph 198 representative of the intensity gradient profile in the region 194. As indicated by the graph 198, the boundary is under-segmented due to a lack of image gradient support. As depicted in the image 193, a region 200 with good reinforcement between the boundary segmentation prediction and the region segmentation prediction is indicated by the marker 202. The good reinforcement in the region 200 is indicated by the graph 204 representative of the intensity gradient profile in the region 200. In certain embodiments, text indicating the lack of reinforcement and/or good reinforcement may be indicated on the image 193 similar to FIG. 13.

Figure 17:
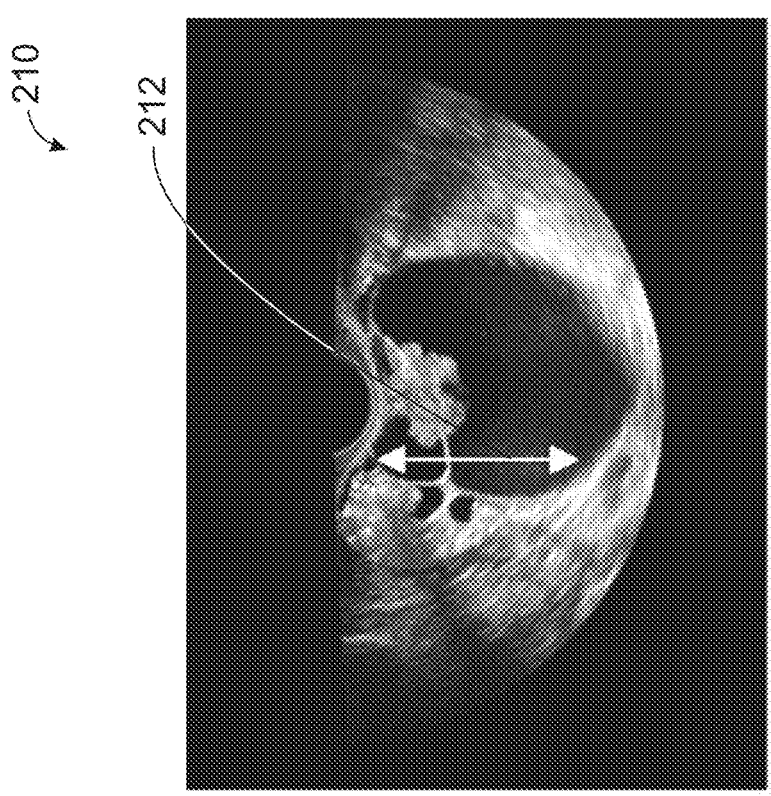
FIG. 17 is an example of an ultrasound image with a caliper location properly placed (e.g., pair of calipers for solid portion of lesion measurement of an ovarian lesion) in accordance with aspects of the present disclosure.
Figure 16:
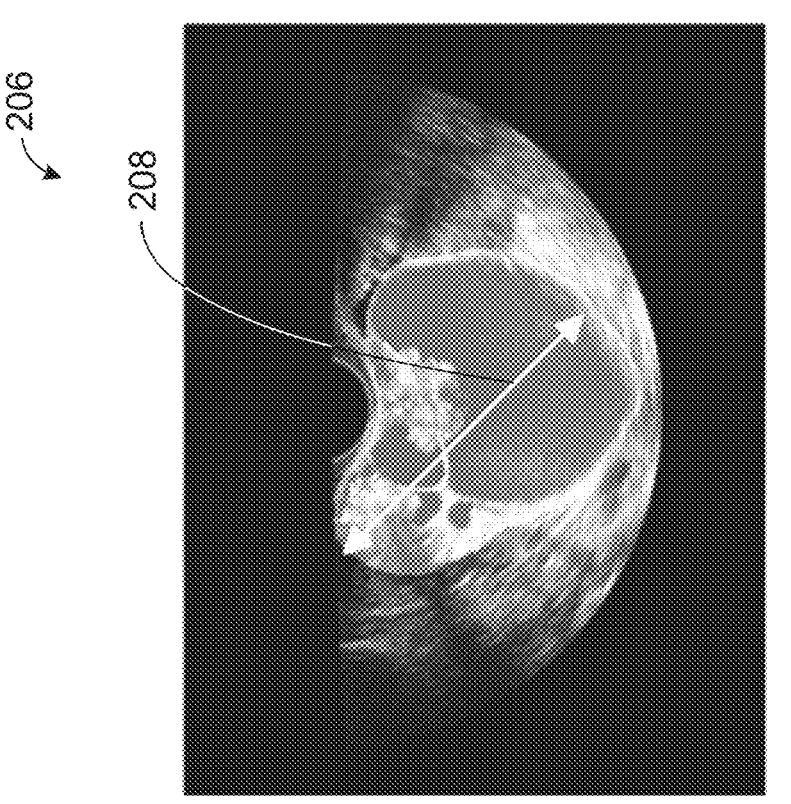
FIG. 16 is an example of an ultrasound image with a caliper location properly placed (e.g., pairs of calipers for lesion diameter measurement of an ovarian lesion), in accordance with aspects of the present disclosure.

FIGS. 16 and 17 are examples of ultrasound images with a caliper location properly placed. The ultrasound images in FIGS. 16 and 17 are from a trans-vaginal ultrasound scan of an ovarian tumor or lesion. FIG. 16 is an ultrasound image 206 of the ovarian lesion having a pair of calipers 208 marked or placed on the ultrasound image 206 to measure the largest cross-section of the ovarian lesion. FIG. 17 is an ultrasound image 210 of the ovarian lesion having a pair of calipers 212 marked or placed on the ultrasound image 210 to measure the largest cross-section of the solid portion of the ovarian lesion. The pair of calipers 208, 212 in the images 206, 210 were are automatically placed in regions high reinforcement as determined by characterization techniques described above. In certain embodiments, one or more of the pairs of calipers 208, 212 may have been adjusted from an initial caliper placement by the user. As noted above, in certain embodiments, the user can overrule the automatic placement of the pair of calipers 208, 212.

Technical effects of the disclosed embodiments include providing systems and method to enable the uncertainty on the boundary of a region of interest in an ultrasound image to be characterized and to be indicated to the user so that a pair of calipers can be properly located (e.g., automatically or manually) to improve workflow and to provide better patient outcomes. In addition, the uncertainty is determined in a faster manner and more accurately.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

This written description uses examples to disclose the present subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A computer-implemented method for characterizing uncertainty on a boundary of a region of interest, comprising:

inputting, via a processor, an ultrasound image having the region of interest into a trained neural network;

outputting, via the processor, from the trained neural network a first prediction of the boundary of the region of interest and a second prediction of a region segmentation of the region of interest;

determining, via the processor, an uncertainty on the boundary based on mismatch between the first prediction and the second prediction; and automatically placing, via the processor, a pair of calipers on the region of interest in the ultrasound image in an absence of uncertainty on the boundary.

2. The computer-implemented method of claim 1, further comprising providing, via the processor, a user-perceptible indication of the uncertainty when mismatch is present between the first prediction and the second prediction.

3. The computer-implemented method of claim 2, wherein providing the user-perceptible indication of the uncertainty comprises indicating on the ultrasound image any region of uncertainty on the boundary.

4. The computer-implemented method of claim 3, wherein the user-perceptible indication comprises highlighting the region of uncertainty on the ultrasound image.

5. A system for characterizing uncertainty on a boundary of a region of interest, comprising:

a memory encoding processor-executable routines; and a processor configured to access the memory and to execute the processor-executable routines, wherein the processor-executable routines, when executed by the processor, cause the processor to:

input an ultrasound image having the region of interest into a trained neural network, wherein the ultrasound image comprises a pair of calipers marked on the region of interest;

output from the trained neural network a first prediction of the boundary of the region of interest and a second prediction of a region segmentation of the region of interest;

determine an uncertainty on the boundary based on mismatch between the first prediction and the second prediction; and providing an alert to a user when at least a portion of the pair of calipers is placed in a region of uncertainty on the boundary.

6. The system of claim 5, wherein the processor-executable routines, when executed by the processor, further cause the processor to provide a user-perceptible indication of the uncertainty when mismatch is present between the first prediction and the second prediction.

7. The system of claim 6, wherein providing the user-perceptible indication of the uncertainty comprises indicating on the ultrasound image any region of uncertainty on the boundary.

8. The system of claim 5, wherein the processor-executable routines, when executed by the processor, further cause the processor to automatically place a pair of calipers on the region of interest in the ultrasound image in an absence of uncertainty on the boundary.

9. The system of claim 5, wherein the processor-executable routines, when executed by the processor, further cause the processor to provide a user-perceptible indication on the ultrasound image of any end of the pair of calipers placed in the region of uncertainty on the boundary.

10. The system of claim 5, wherein the processor-executable routines, when executed by the processor, further cause the processor to alter placement of the pairs of calipers on the region of interest in the ultrasound image when at least the portion of the pair of calipers is placed in the region of uncertainty on the boundary.

11. A non-transitory computer-readable medium, the computer-readable medium comprising processor-executable code that when executed by a processor, causes the processor to:

input a medical image having a region of interest into a trained neural network, wherein the ultrasound image comprises a pair of calipers marked on the region of interest;

output from the trained neural network a first prediction of a boundary of the region of interest and a second prediction of a region segmentation of the region of interest;

determine an uncertainty on the boundary based on mismatch between the first prediction and the second prediction; and alter placement of the pairs of calipers on the region of interest in the ultrasound image when at least a portion of the pair of calipers is placed in a region of uncertainty on the boundary.

12. The non-transitory computer-readable medium of claim 11, wherein the processor-executable code, when executed by the processor, further causes the processor to provide a user-perceptible indication of the uncertainty when mismatch is present between the first prediction and the second prediction.

*　　*　　*　　*　　*